United States Patent

Dao et al.

Patent Number: 6,066,104
Date of Patent: May 23, 2000

[54] DEVICE FOR CERVICAL AND PELVIC MEASUREMENT IN MEDICAL OBSTETRICS

[76] Inventors: Leland H. Dao, 61-427 Kamehameha Hwy., Haleiwa, Hi. 96712; Christopher S. Miura, 5330 Limu Pl., Honolulu, Hi. 96821; Michael James Bradley, Rd. E Cymbidiam Acres, Volcano, Hi. 96785

[21] Appl. No.: 09/172,781

[22] Filed: Oct. 14, 1998

Related U.S. Application Data

[63] Continuation-in-part of application No. 08/158,688, Sep. 22, 1998, abandoned, which is a continuation of application No. 08/811,030, Mar. 4, 1997, abandoned
[60] Provisional application No. 60/012,836, Mar. 5, 1996.

[51] Int. Cl.$^7$ .................................................. A61B 5/103
[52] U.S. Cl. .............................................................. 600/588
[58] Field of Search ................................... 600/551, 587, 600/588, 591

[56] References Cited

U.S. PATENT DOCUMENTS 4,207,902 6/1980 Krementsov .
4,245,656 1/1981 Farr et al. .
4,362,167 12/1982 Nicolai et al. .
4,611,603 9/1986 Kelso et al. .
4,682,609 7/1987 Parsons .
4,719,925 1/1988 Parsons .

*Primary Examiner*—Cary O'Connor
*Assistant Examiner*—Pamela L. Wingood
*Attorney, Agent, or Firm*—Lyon & Lyon LLP

[57] ABSTRACT

A device for measuring cervical dilation includes a glove having middle finger an index finger, a thumb, and a palm area. A tube is attached to the index finger and extends from near the tip of the index finger along the length of the index finger towards. A calibrated line has a first end attached near the tip of the index finger and extends through the tube. The calibrated line has a second end attached to the thumb, or hangs free with a tether handled. A latch adjacent the palm area prevents unintended movement of the calibrated line. In another embodiment, an indicator arm has a first end attached to the middle finger. A flexible gauge arm is attached to the index finger. A gauge attached to the gauge arm is positioned adjacent to the palm area, and has calibrated markings. The second end of the indicator arm overlays the gauge. In a third embodiment, a meter rod has a first end within a guide tube. A measuring line is attached to the meter rod and extends out of the first end of the guide tube. The meter rod may optionally be linked to a potentiometer and a visual display and/or a microprocessor.

29 Claims, 12 Drawing Sheets

DEVICE FOR CERVICAL AND PELVIC MEASUREMENT IN MEDICAL OBSTETRICS

CROSS-REFERENCES TO RELATED APPLICATIONS

This application is a continuation-in-part of U.S. patent application Ser. No. 08/158,688 filed Sep. 22, 1998 now abandoned by Leland Dao, Express Mail No. EM350827628US, which is a continuation of U.S. patent application, Ser. No. 08/811,030 filed Mar. 4, 1997, now abandoned, which is a continuation-in-part application claiming the benefit of U.S. Provisional Application, Ser. No. 60/012,836 filed Mar. 5, 1996, each of these references incorporated herein by reference.

BACKGROUND OF THE INVENTION

The present invention relates to devices used for measuring and monitoring the female cervix and pelvis in the field of Medical Obstetrics.

The assessment of the cervix during pregnancy, labor and delivery is an important part of Obstetrical monitoring. This measurement can affect whether the patient is considered ready for delivery or is sent home with a diagnosis of false labor. Still, labor and delivery room personnel generally continue to rely on blind palpatory estimations for measurements of cervical dilation.

In practice, a person intending to perform a cervical measurement places a sterile glove on their hand, and extends their index and middle fingers into the patient's vagina. Once the cervix is palpated, the cervical os is located with the examining finger tips which are spread apart or abducted. The degree of opening of the cervical os is usually blindly assessed merely by the spacing between the index and middle fingers.

The generally accepted scale ranges from zero to ten (centimeters or points). This form of cervical monitoring is based purely on a sense of feel without any visual aspect. A finding of cervical dilation of less than three centimeters may warrant the physician to send the pregnant patient home. Should the clinician estimate a cervical measurement of greater than three centimeters, the patient is usually diagnosed as being in labor, and routinely is monitored through the completion of delivery. Throughout this monitoring period, the patient may receive several more manual cervical exams to evaluate the progression of labor. When the patient is measured to be ten centimeters or greater, she is diagnosed as having complete cervical dilation, and then is encouraged to push the baby out. Prior to the attainment of a completely dilated cervical measurement, patients are encouraged not to push yet, for risk of premature delivery and harm to both mother and baby.

It is apparent that the cervical measurement is of critical importance in diagnosing labor, yet using current practices there is a large potential for subjective variation and error. As cervical dilation is in essence simply measured by feel, a cervical and pelvic birth canal examination and measurement could vary greatly, depending upon the level of experience, knowledge and skill of the examiner. If the cervical dilation is measured inaccurately, the patient may potentially be misdiagnosed, and be subject to improper care.

During the initial evaluation of a pregnant patient there are several important measurements that must be obtained to ensure a normal delivery. This includes the measurement of the pelvic conjugate diameter, a sizing estimation used to determine the size adequacy of the mother's pelvic canal for a normal vaginal delivery. This again is roughly estimated manually during the sterile glove exam, by using the length of the index finger to measure the distance between the posterior coccyx and anterior pubic ramous. Should pelvic inadequacy be determined during this exam (i.e., the mother's canal is too small or the baby too large) an elective Cesarean section may be planned. This measurement, if performed more accurately and reliably, could potentially avoid improper early decisions pertaining to the pregnancy.

Although various devices have been proposed for more reliably measuring cervical dilation, none have achieved widespread acceptance apparently due to their cost, complexity and inconvenience. For example, most devices have been cumbersome and difficult to read during normal field conditions, and generally considered inoperable during darkened field conditions. Accordingly, there is a need for a more accurate means of cervical and gravid pelvic examination, that produces objective, visually interpreted measurements of the cervix and pelvic birth canal as may be desired during pregnancy, labor and delivery.

SUMMARY OF THE INVENTION

To these ends, a device for measuring cervical dilation preferably includes a glove having middle finger an index finger, a thumb, and a palm area. A tube is attached to the index finger and extends from near the tip of the index finger along the length of the index finger. A calibrated line is most desirably attached near the tip of the index finger and extends through the tube. A latch adjacent the palm area may be provided for preventing inadvertent movement of the calibrated line. By abducting the fingers, an accurate measurement of dilation is obtained.

In a second aspect, a device for measuring cervical dilation preferably includes a flexible indicator arm having a first end attached to the middle finger. A flexible gauge arm is advantageously attached to the index finger. A gauge is attached to the gauge arm and positioned adjacent to the palm area. The second end of the indicator arm overlays the gauge and indicates the amount of dilation.

In a third aspect, a meter rod preferably has a first end within a guide tube, and a measuring line attached to the meter rod and extending out of the guide tube. Rings are preferably included at one end of the measuring line. The meter rod may optionally be linked to an electronic measuring device, such as a potentiometer, that translates the physical measurement to an electrical signal. This electronic data may then be presented to the examiner via a visual device, such as a digital display, and/or inputted into another electrical device such as a microprocessor. In this manner, the present invention may actually be a component of an operating system capable of analyzing, for example, the extent of dilation and/or the progress of labor. Other and further objects and advantages will appear hereinafter.

DESCRIPTION OF THE DRAWINGS

In the drawings, wherein similar reference characters denote similar elements throughout the several views.

DETAILED DESCRIPTION OF THE DRAWINGS

Figure 1:
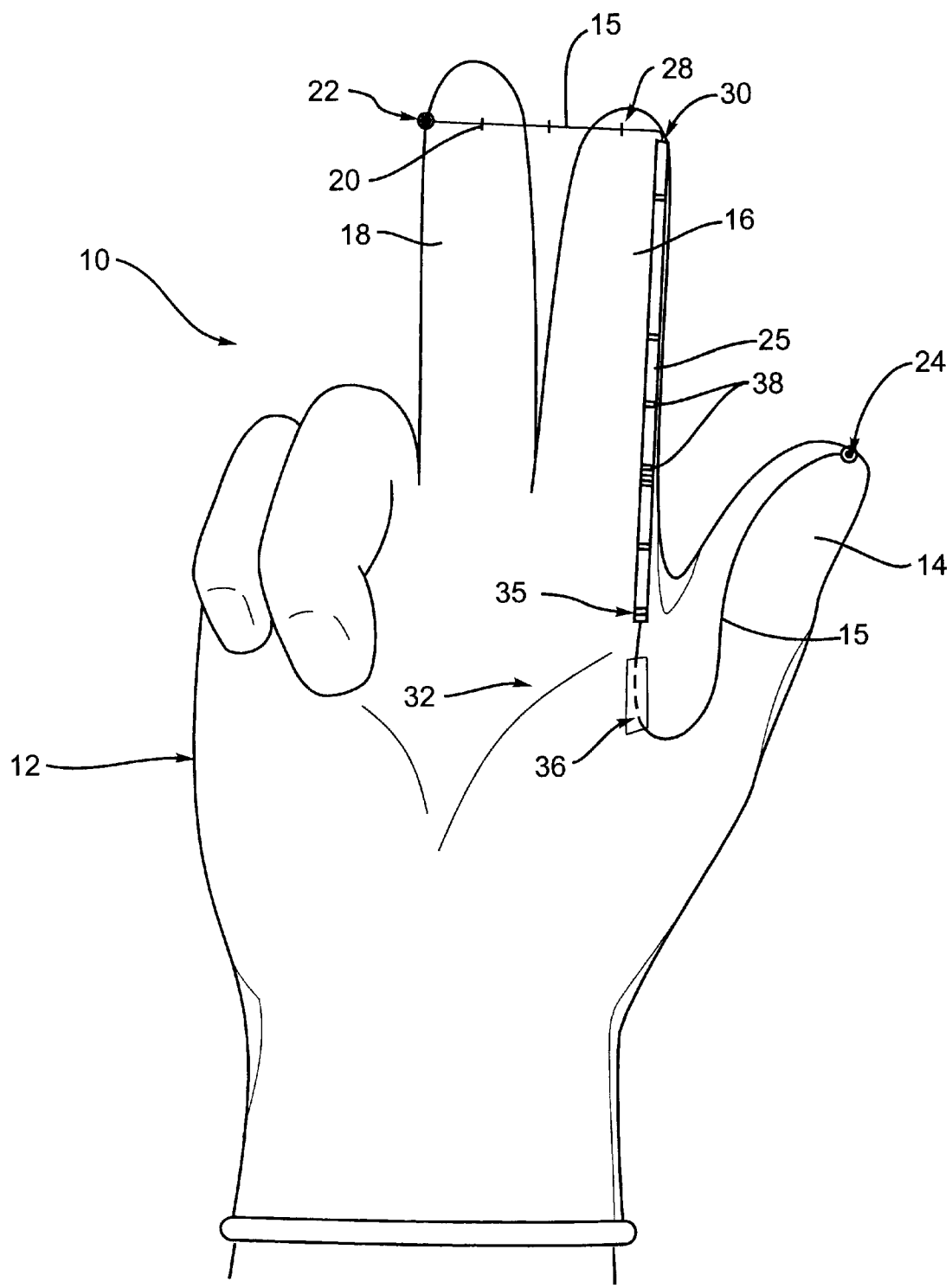
FIG. 1 is a front view of a first embodiment cervical measuring device using the string measure attached to the thumb of the glove.

As shown in FIG. 1, a first embodiment 10 has an incrementally calibrated measuring string 15 or any suitable line material, and a calibrated linear tube 25 all of which may be attached to a hand shaped medical glove 12. The measuring string 15 is marked with centimeters or other unit measure. One end of the measuring string 15 is permanently attached to the tip of middle finger 18.

When properly positioned, the origin 22 or attachment point of the measurement string line 15 is on the distal, anterior, and lateral surface of the middle finger 18 of the glove embodiment. From the origin 22, the string traverses toward the tip 28 of the index finger 16 and enters the front or top end opening 30 of the calibrated tube 25.

The tube 25 has a hollow central bore through which the measuring string 15 passes. The tube 25 starts at the tip 28 of the lateral surface of the index finger 16, and is attached parallel to and along the lateral edge of the index finger 16 of the glove 12. The tube 25 ends where the index finger 16 joins the palm 32.

When the front end 30 of the tube 25 is placed on the presenting part of the fetus (usually the fetal scalp), a measurement may be obtained of the obstetrical station of labor, from the corresponding calibrated markings 38 on the tube 25. These calibrated markings 38 can also be used to measure the adequacy of pelvic conjugate diameter during labor.

Figure 2:
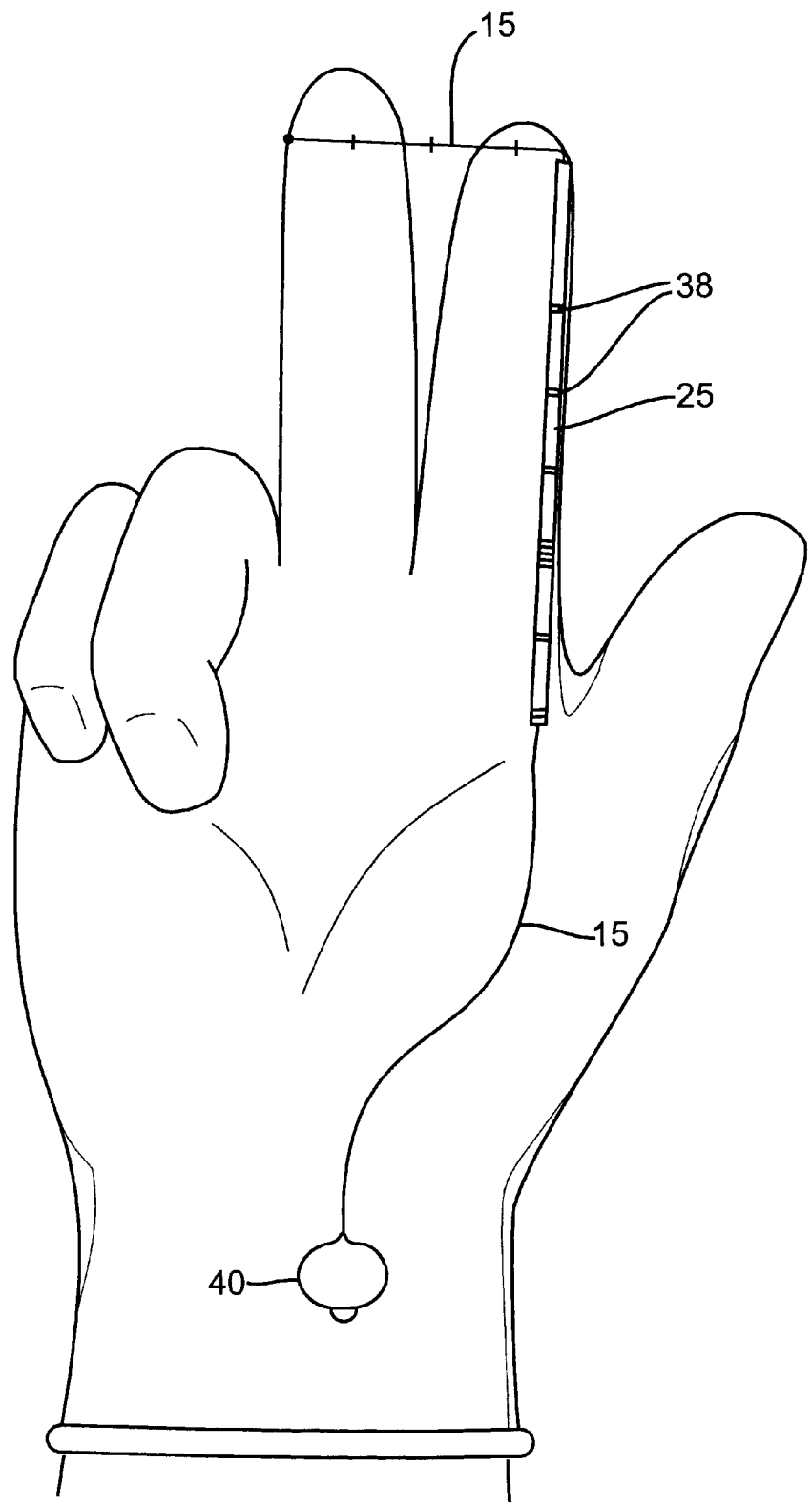
FIG. 2 is a front view of a second embodiment cervical measuring device using a tethered measuring string and handle.

The measuring string 15 passes through the bore of the tube 25 and out of the back end 35 of the tube 25 to either attach to the distal tip of the thumb 24, or remain freely hanging with a tether handle 40, as shown in FIG. 2.

During a cervical examination, when the middle 18 and index 16 fingers of the measuring hand are spread apart or abducted, the measuring string will mark out to the width of dilation of the fingertips, and, depending upon the calibration marking system used, will correlate to a point on the measuring string. One area of calibrated measurement reading may be on the distal or front end of the tube 25 at opening 30. Another area of measurement reading may be the proximal end 35 of the tube. Both areas may be used simultaneously for the purposes of this configuration. The thumb or unattached side of the measuring string 15 can be pulled, with the fingers together, to zero the string 15 for repeated measurements.

Interval unit markings 20 (e.g., centimeters) begin at or near the origin 22 of the string, and continue along the length of the measuring string 15. This form of unit markings provides a direct measure, and the reading is made at the distal tip 30 of the tube. Alternatively the unit markings 20 of the measuring string 15 are on the proximal end 35 of the tube 25, thus calibrated to correlate to a corresponding measurement found on the measuring fingers. This proximal-end measuring design may contain a securing slot or latch 36 that can secure the measuring string at a measured point when so desired. This prevents errors in measurements due to spreading the fingers after they are removed from the cervix.

Figure 3:
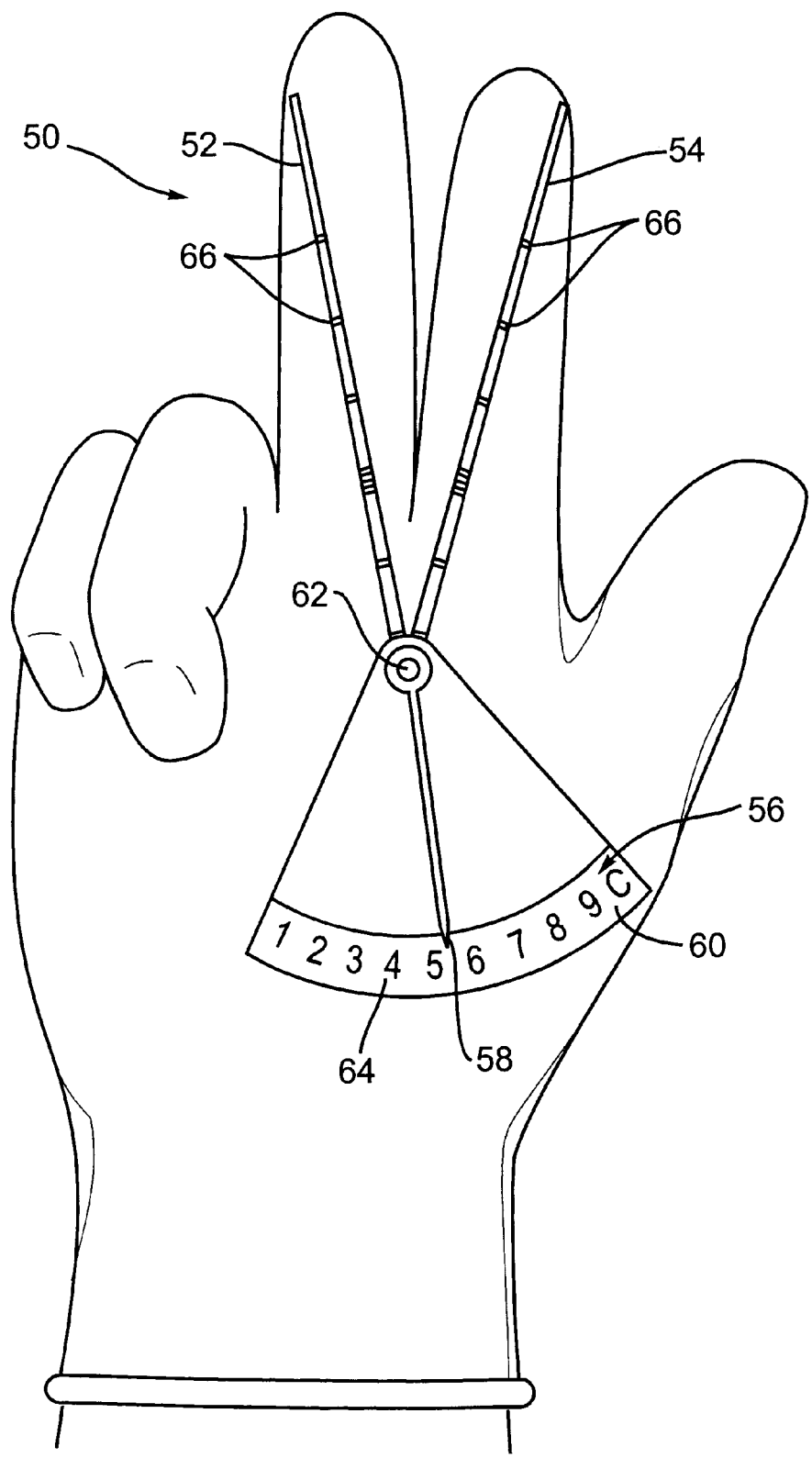
FIG. 3 is a front view of a third embodiment cervical measuring device using measuring arms and an indicator gauge.

As shown in FIG. 3, a third embodiment 50 has two linear measuring arms 52 and 54, and an indicator gauge 56, attached to a medical glove 12 or the device user's hand. The first measuring arm 52, adjacent to the lateral surface of the middle glove finger 18, tapers and flattens to form a gauge pointer 58 over the gauge. The second measuring arm 54 adjacent to the lateral surface of the index finger 16 forms a planar gauge face 60.

The distal or front ends of the measuring arms may be attached to the lateral sides of the index 16 and middle 18 fingers of a medical or surgical glove 12, which is shown as a right handed glove. The flexible measuring arms pivotably intersect one another in their midshaft regions at an axis point 62. The first arm 52 lies above the planar surface of gauge face 60 near the axis point. The first arm 52 and gauge face 60 form a measurement indicator. The face of the measuring gauge contains calibrated markings 64 which are proportionate to units of cervical dilation.

In use, the width of abduction of the measuring fingers and adjacent measuring arms is proportionate to the measurement reading of the indicator arm on the gauge face. In particular, the proportions of distances of the measuring arms 52, 54 and the measuring gauge 60 create specific proportions by which the cervical reading is obtained. Hence, the position of the measuring arms 52, 54 is translated onto a calibrated gauge that accurately displays the degree or measurement of the cervical dilation. Both of the measuring arms distal from the gauge face may contain calibrations 66 that may be used to obtain measurements of pelvic adequacy as well as information pertaining to degree of station of the fetal presenting part.

Figure 4:
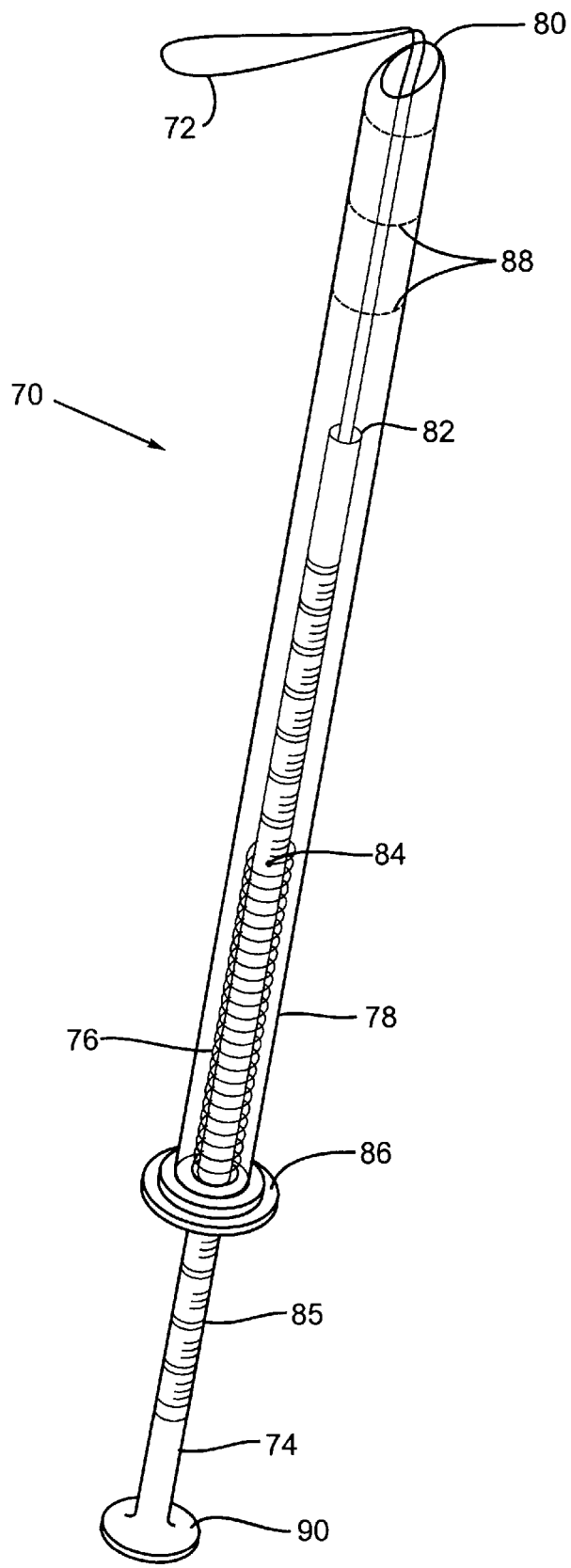
FIG. 4 is a perspective view of a fourth embodiment.

In a fourth embodiment, as shown in FIG. 4, an Obstetrical measuring device 70 includes a loop 72 of measuring line, a measuring rod 74, and optionally an expansion spring 76, within a guide tube 78. The measuring loop line 72 protrudes from the front end 80 of the guide tube 78, and is attached to the front end 82 of the meter rod 74. If used, the spring 76 is attached to the back or back end 86 of the guide tube 78, and at a midsection 84 of the meter rod 74. The spring tension regulates the movement of the meter rod 74, and thus also standardizes the finger movement force within the loop line 72.

Figure 5:
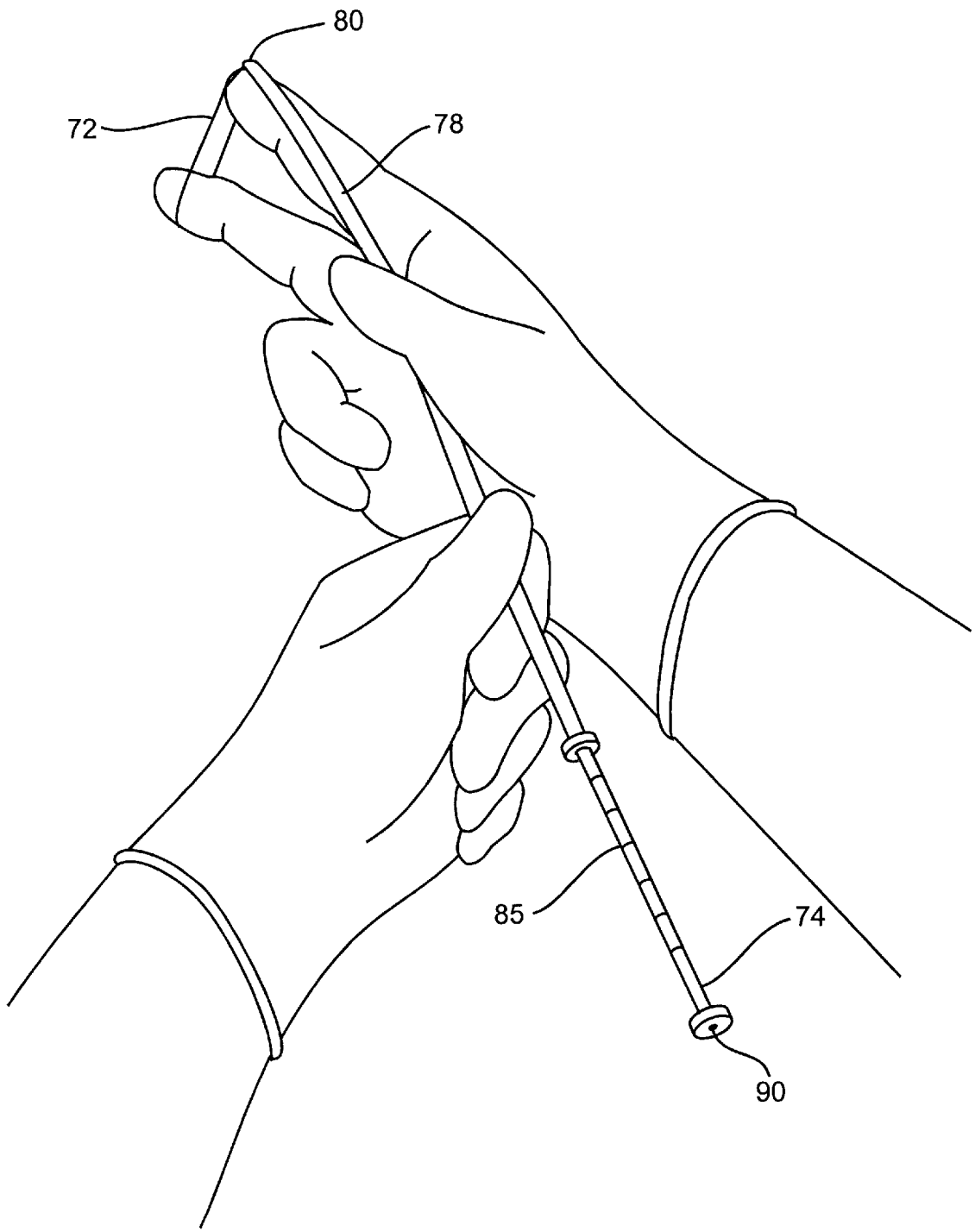
FIG. 5 is a perspective view of the embodiment of FIG. 4 in use.

To use the device 70, the index and middle finger tips are placed within the measuring loop line 72 as shown in FIG. 5. When the loop of line 72 is stretched or expanded by spreading the fingers apart, the calibrated meter rod 74 correspondingly moves to display the degree of measuring line expansion. The measurement of cervical dilation is read from measurement markings 85 on the metering rod 74, at the rim 86 at the back end of the guide tube 78, or elsewhere on or in the guide tube 78. The guide tube 78 also contains calibrations 88 which may be used for pelvic conjugate diameter measurements. A cap 90 at the back end of the tube 78 prevents the metering rod 74 from moving completely into the guide tube 78.

Figure 6:
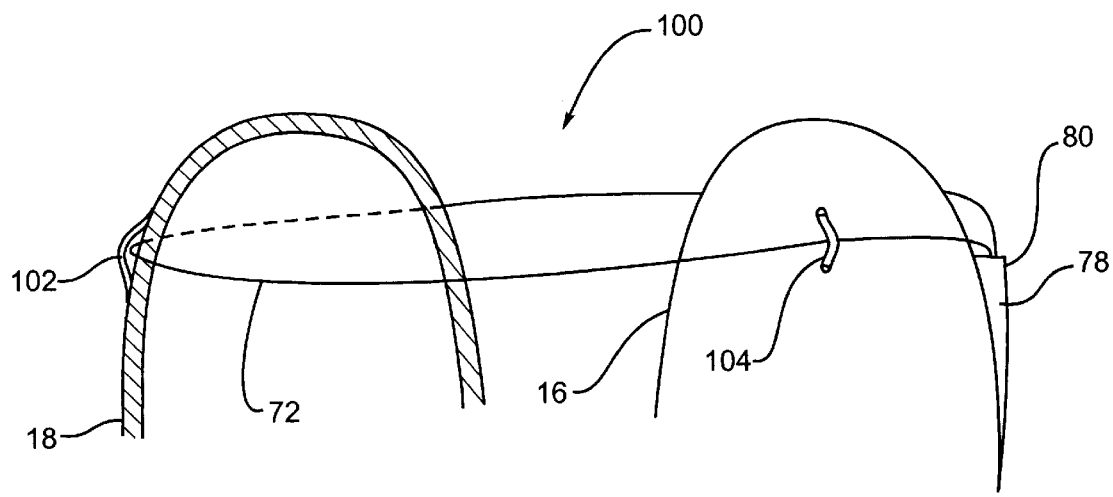
FIG. 6 is partial front view in part section of a fifth embodiment.

In a fifth embodiment, as shown in FIG. 6, a glove 12 has a small eyelet 102 located on the tip of the middle finger 18.

The measuring line 72 is looped through the eyelet 102. The index 16 and middle 18 glove finger tips are placed within the measuring loop line 72. An eyelet 104 keeps the loop line 72 in position at the tip of the index finger 16. When the loop of line 72 is expanded by finger abduction, the attached meter rod 74 moves to display the corresponding degree of measuring line expansion. When the fingers are within the loop line and inserted into the cervix and abducted for measurement, the loop line 72 expands and pulls the calibrated meter rod 74, creating the appropriate measurement which can be read from the markings 85 at the rim 86 as described above with reference to FIGS. 4 and 5.

Figure 7:
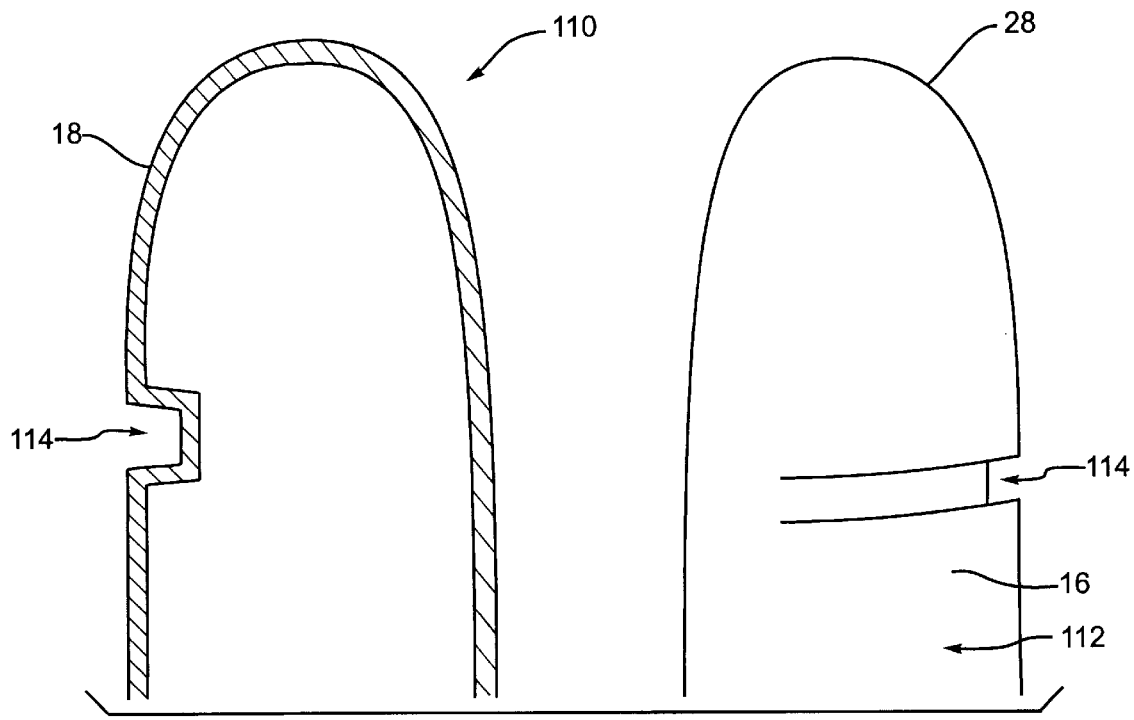
FIG. 7 is a partial front view in part section of a sixth embodiment.
Figure 8:
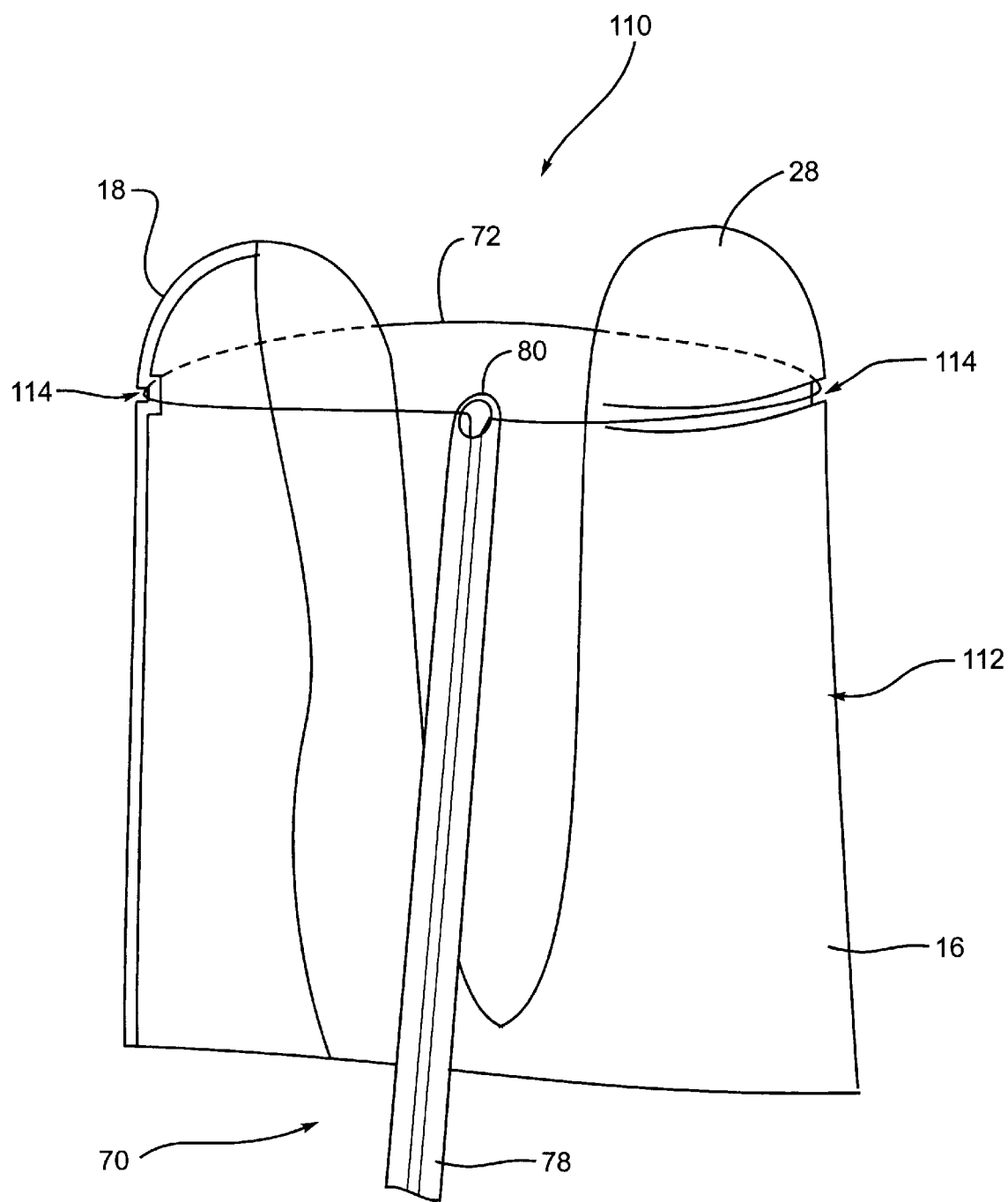
FIG. 8 is a perspective of the embodiment of FIG. 7 in use.

In a sixth embodiment 110, as shown in FIG. 7, a specially designed glove 112 has grooved finger tip guides. The device 70, shown in FIGS. 4 and 5, may be unattached and separate from the glove 112, while still using the loop measuring line 72 system. The glove 112 has specifically formed middle and index finger guides 114 which accommodate the loop line 72 during measurement, and prevent slippage off the glove finger tips. When the glove fingers are inserted into the cervix and abducted for measurement, the loop line 72 is guided along the guides or grooves 114 and measurement line movement is translated through the calibrated meter rod, creating the appropriate measurement. With the device 70, the lateral position of the guide tube 78 can be along side the index finger 16, as shown in FIG. 5, or between the index 16 and middle 18 fingers, as shown in FIG. 8, or at other positions, so long as the front or distal end 80 of the tube 78 is near the finger tips. The glove 12 and 112 may be provided in different sizes, and can be used in place of conventional latex surgical gloves now widely used in obstetrics. Use of the gloves 12 and 112 with any of the embodiments described is not distinguishable to the patient from use of a conventional glove.

Figure 9:
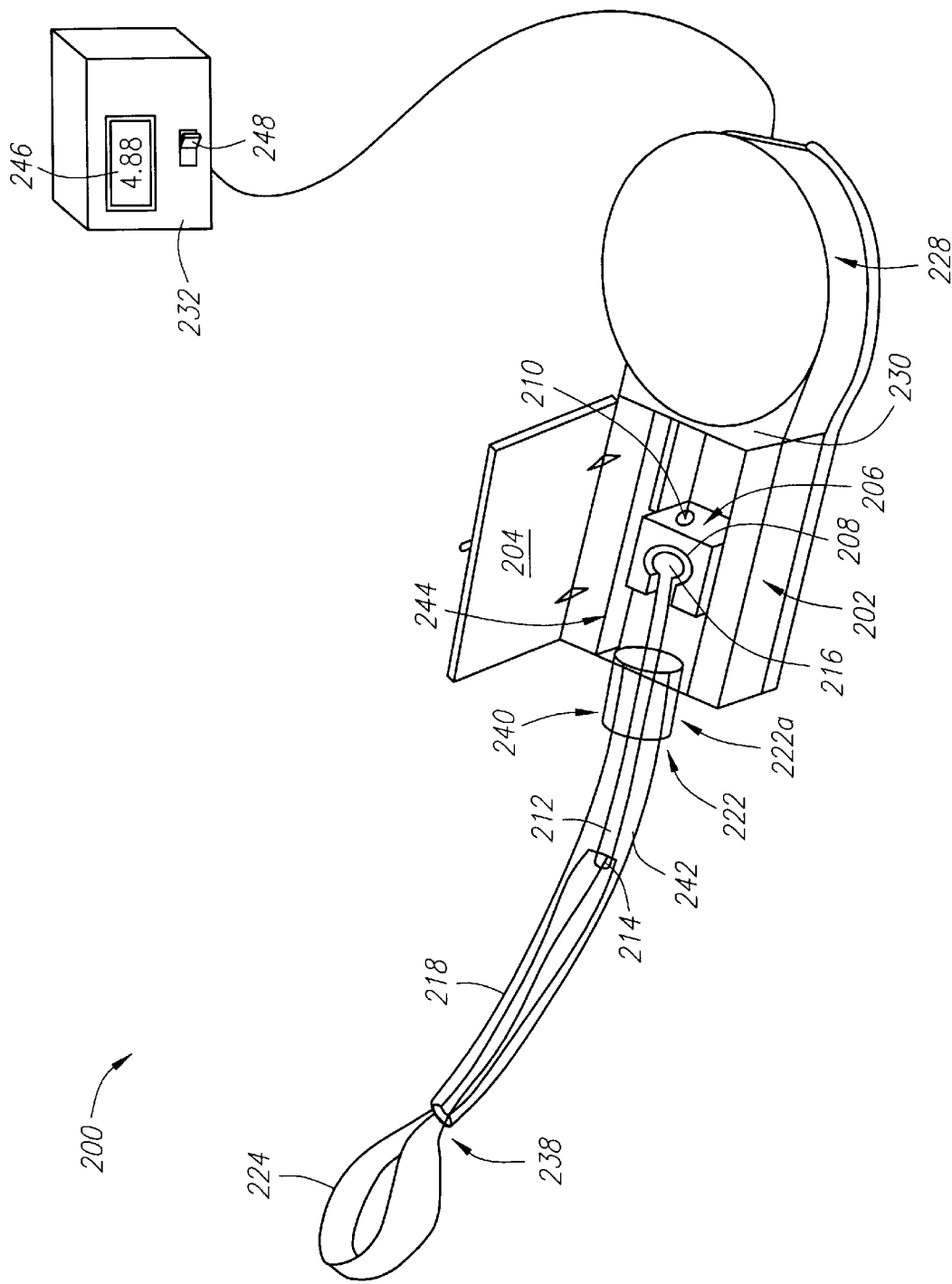
FIG. 9 is a perspective view of a seventh embodiment.

Similar to the embodiment shown in FIGS. 4 and 5, a seventh embodiment of an Obstetrical measure device 200, as shown in FIG. 9, includes a loop of measuring line 224, a meter rod 212, and a flexible guide tube 218. The measuring loop line 224 protrudes from the front end 242 of the guide tube 218 and is attached to the front end 242 of the meter rod 212 via a connecting hook 214. The meter rod 212 may optionally be linked to an electronic measuring device 228, such as a potentiometer, that translates the physical measurements taken by the examiner to an electrical signal.

FIG. 9 shows an electronic measuring device 228 mounted to one end of a latch box or housing 202 having a hinged cover 204. The electronic measuring device 228 is preferably a position transducer such as the 5 K ohm potentiometer for a 5" linear measurement manufactured by Space Age Controls, Model No. 175-0401. A payout line or string 230 of the potentiometer 228 is attached to a catch 206 via a payout line 224 holder. The catch 206 is slidably mounted within a retention portion 202a of the housing 202. The catch 206 includes a recessed area or socket member 208 configured to receive a bead or ball member 216 at the rear end 244 of the meter rod 212. The rear end 240 of the guide tube 218 is mounted to the housing 202 opposite the potentiometer 228 via a guide tube connector 222.

Figure 11:
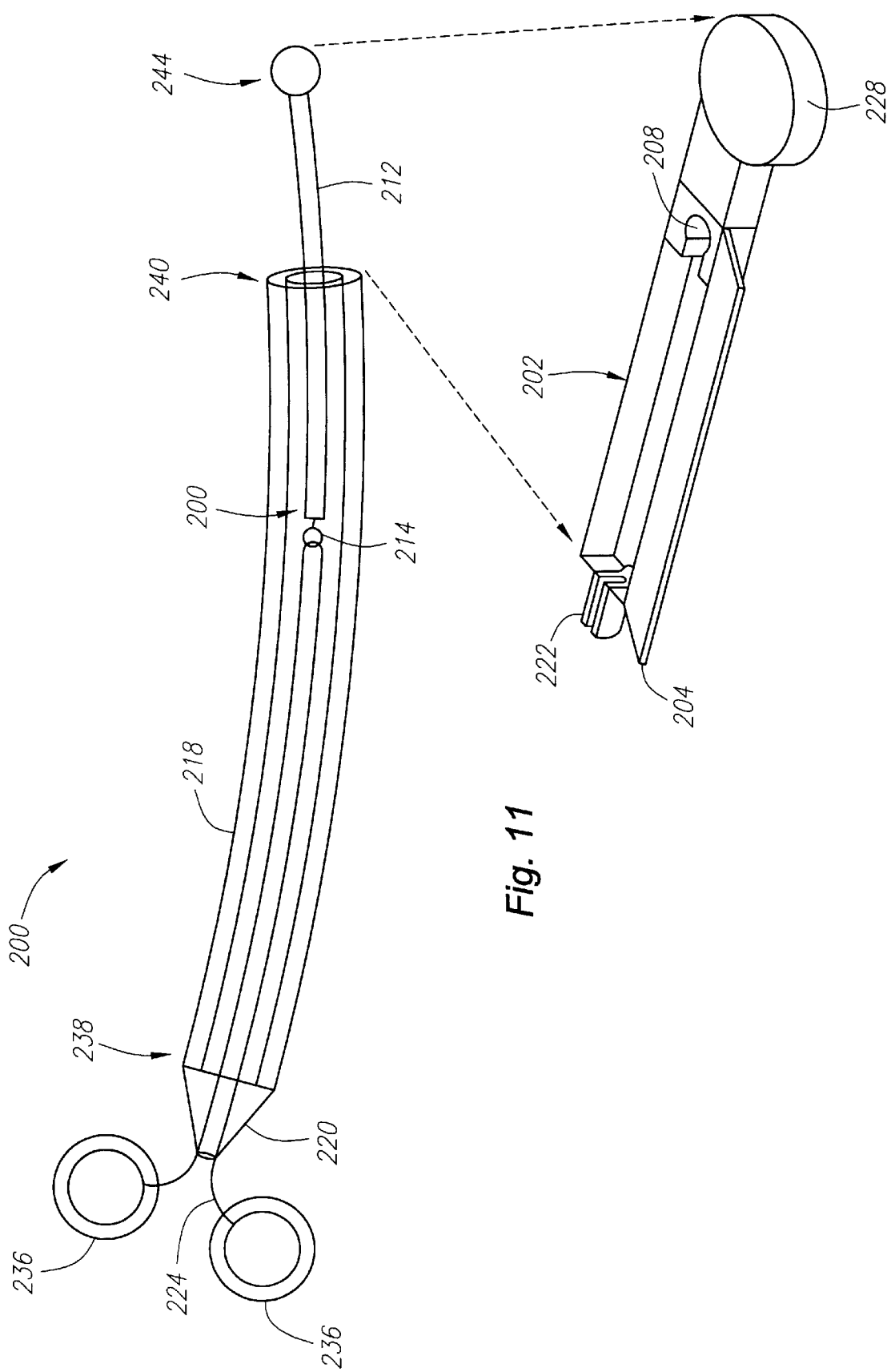
FIG. 11 is an exploded perspective view of a ninth embodiment.

The guide tube connector 222 may comprise a bushing 222a and a slot 222b where the slot 222b is adapted to receive the guide tube 218 and the bushing 222a is adapted to wrap around and hold the guide tube 218 in place within the slot 222b. The slot 222b may be separate or integral with the housing 202. FIGS. 9 and 11 illustrate the guide tube connector 222 disposed outside of the housing 202. However, for additional support, the guide tube connector 222 may be positioned inside of the housing 202. The guide tube 218, measuring line 224, and meter rod 212 are each made from a disposable material such as plastic or rubber. In this manner, the guide tube/measuring line/meter rod assembly 238 advantageously avoids the introduction of bacteria into the vagina and uterus due to its one-time-use.

In use, the tips of the index and middle fingers are placed within the measuring loop line 224 as shown in FIG. 5. When the loop of line 224 is stretched or expanded by spreading the fingers apart, the meter rod 212 is drawn away from the housing 202, causing the catch 206 to slide toward the guide tube connector 222 and the string 230 to be pulled away from the potentiometer 228. As the amount of dilation corresponds to the length of string 230 being paid out, the potentiometer 228 can be calibrated to a corresponding measurement taken by the examiner and convert this physical measurement of cervical dilation to an electrical signal.

Once there is an electrical quantity that translates to a physical measurement, it can then be presented via visual devices and/or inputted into another electrical device such as a microprocessor. For example, the measurements can be time-stamped and logged and then fed into the various devices that comprise the microprocessor. In this manner, the present embodiment may actually be a component of an operating system capable of analyzing, for example, the extent of dilation and/or the progress of labor.

As shown in FIG. 9, the potentiometer 228 is in communication with a visual device 232. The visual device 232 is preferably a digital display such as a MODUTEC digital panel meter. The digital display 232 includes an illuminated readout 246. To this end, the embodiment shown in FIG. 9 allows the examiner to advantageously operate the measuring device 200 even during darkened field conditions.

Once the examiner has taken the measurement and read it on the digital display 232, the examiner opens the cover 204 of the housing 202 in order to pull out and dispose of the guide tube/measuring line/meter rod assembly 238. Depending on the stage of labor, the examiner may choose not to flip the on/off switch 248 of the digital display 232 to the off position. Should the examiner need to take another measurement, a new disposable the guide tube/measuring line/meter rod assembly 238 is inserted into the socket member 208 of the catch 206 and the process is repeated.

Figure 10:
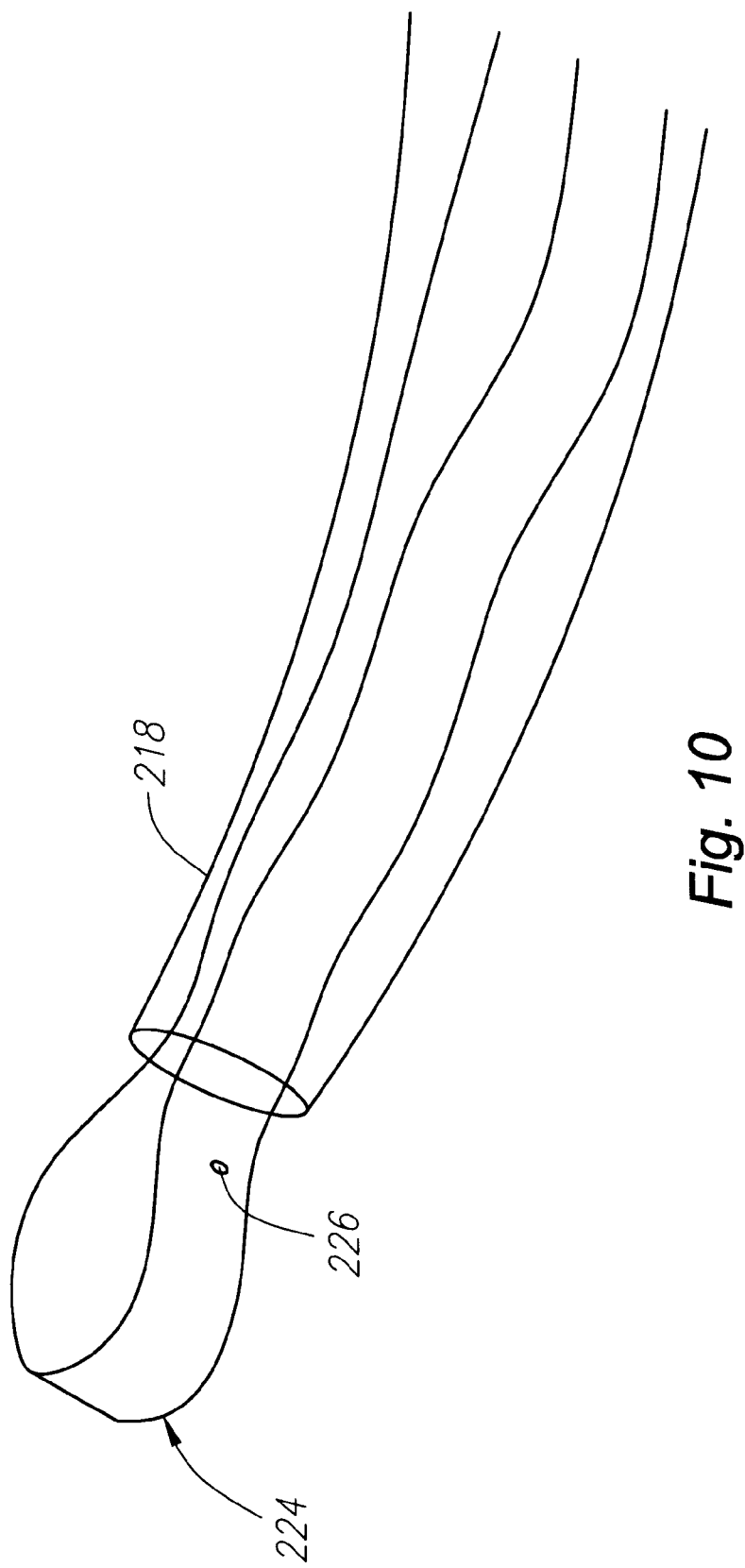
FIG. 10 is a partial perspective view of an eighth embodiment.

As shown in FIG. 10, the measuring line 224 may optionally include a stitch 226 or the like through the loop of the measuring line 224. In this manner, the measuring line 224 is adapted to frictionally engage the finger tip so that it is less likely to slip out during use. In use, once the middle finger tip, for example, is inserted between the stitch 226 and the inner circumference of the loop formed in the folded end of the measuring line 224, the index finger tip is inserted between the folds of the measuring line 224 next to the guide tube 218. As the fingers are abducted to take the measurement, the middle finger tip is held in place, whereas the index finger tip is allowed to travel along the inside of the folds of the measuring line 224.

Figure 12:
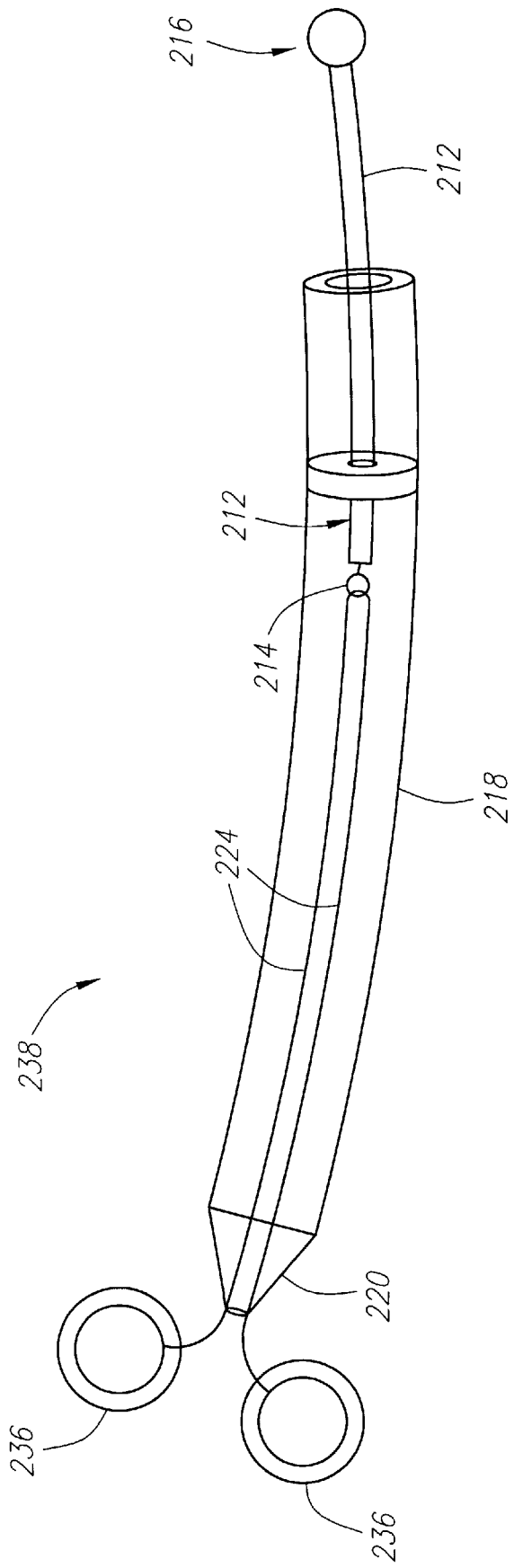
FIG. 12 is a partial perspective view of the embodiment of FIG. 11 with a stopper.
Figure 13:
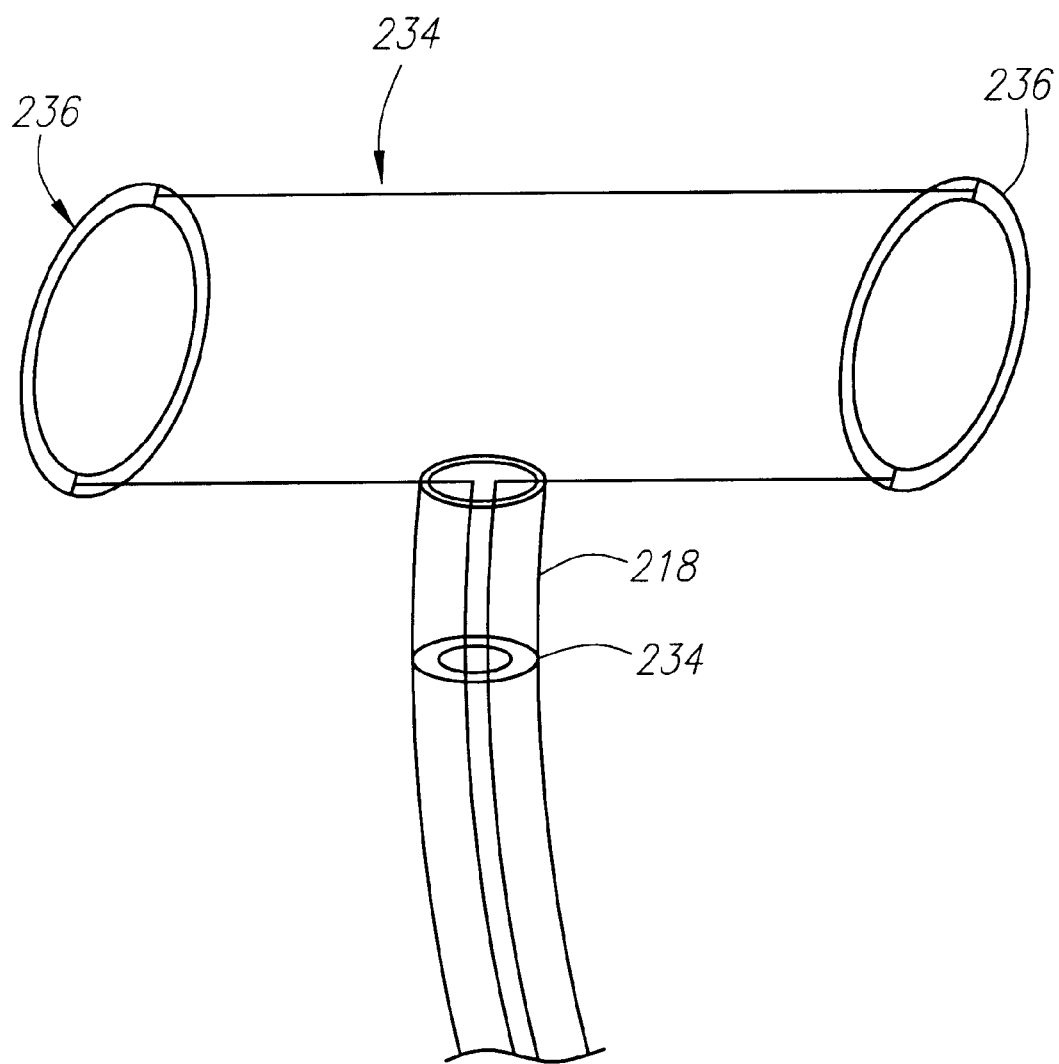
FIG. 13 is a partial perspective view of a tenth embodiment.

As shown in FIGS. 11–13, the measuring line 224 may optionally be adapted to accommodate the tips of both the middle finger and the index finger by attaching the measuring line 224 to a pair of rings 236. As best seen in FIG. 13, the rings 236 may be hollow for receiving a measuring line 224 threaded therethrough. While the measuring line 224 is shown as being a single line, the measuring line 224 may comprise multiple lines. However, a single line has been found to work more efficiently, similar to that of a pulley, and hence improve the ease with which a measurement may be taken. In use, the middle and index finger tips are respectively inserted into one of the rings 236. The rings 236 advantageously keep the finger tips from slipping out when they are spread apart for taking a measurement. As the fingers are abducted, the measuring line 224 pulls against the connecting hook 214, causing the meter rod 212, catch 206, and string 230 to be drawn away from the housing 202. Once the potentiometer 228 converts the physical measurement to an electrical signal, the examiner may read the measurement on a computer screen, digital display 232 (shown in FIG. 9), or the like.

As shown in FIGS. 11–12, the guide tube 218 may optionally include a coned tip 220 at its front end 238. The coned tip 220 keeps the measuring line 224 centered within the tube 218 for a more accurate measurement, particularly when the double ring configuration is being used.

As shown in FIGS. 12–13, a stopper 234 may optionally be included to prevent the measuring line 224 and/or meter rod 212 from being pulled through the guide tube 218. FIG. 12 shows the stopper 234 proximate the rear end 240 of the guide tube 218 for preventing the meter rod 212 from being pulled through the guide tube 218, whereas FIG. 13 shows the stopper 234 proximate the front end 238 of the guide tube 218 for preventing the measuring line 224 from being pulled through the guide tube 218. Due to the double ring configuration, however, the stopper 234 at the front end 238 of the guide tube 218 may be unnecessary as the rings 236 themselves would act as a stopper 234. While not shown in FIGS. 10–11, stopper 234 may optionally be included to prevent the measuring line 224 and/or meter rod 212 from being pulled through the guide tube 218. In contrast to the double ring configuration, stopper 234 at the front end 238 of the guide tube 218 is preferred for preventing the measuring line 224 from being pulled through the guide tube 218.

Thus, while several embodiments have been shown and described, many modifications and substitutions of equivalents may be made without departing from the spirit and scope of the invention.

What is claimed is:

1. A device for measuring cervical dilation comprising:
   a guide tube having a first end and a second end;
   a meter rod having a first end within the guide tube, and a second end;
   length markings on the meter rod; and
   a loop line attached to the meter rod and extending out of the first end of the guide tube.

2. The device of claim 1, further comprising a spring attached to the guide tube and to the meter rod.

3. The device of claim 1, further comprising a rim at the second end of the guide tube, and a cap on the second end of the meter rod.

4. A device for measuring cervical dilation comprising:
   a glove having an index finger including an index finger tip and a middle finger including a middle finger tip;
   a first loop guide or eyelet on the index finger tip;
   a second loop guide or eyelet on the middle finger tip;
   a guide tube;
   a metering rod extending partially within the guide tube;
   length markings on the metering rod; and
   a loop line attached to the metering rod and extending out of the guide tube and through the first and second loop guides.

5. The device of claim 4, wherein the guide tube is attached to the index finger.

6. A device for measuring cervical dilation comprising:
   a guide tube having a first end and a second end;
   a meter rod having a first end within the guide tube, and a second end;
   a measuring line attached to the meter rod and extending out of the first end of the guide tube; and
   an electronic measuring device linked to the second end of the meter rod.

7. The device of claim 6, further comprising a visual display in communication with the electronic measuring device.

8. The device of claim 6, wherein the measuring line is stitched near the first end of the guide tube for receiving a finger tip.

9. The device of claim 6, further comprising a first ring and a second ring, each ring attached to the measuring line near the first end of the guide tube for respectively receiving a finger tip.

10. The device of claim 9, wherein each ring is hollow for threadably receiving the measuring line, and wherein each ring respectively receives one of an index finger tip and a middle finger tip.

11. The device of claim 9, wherein the first end of the guide tube includes a coned tip.

12. The device of claim 6, wherein the second end of the meter rod includes a connecting ball.

13. The device of claim 12, further comprising a housing and a catch slideably mounted within the housing, wherein the catch is adapted to receive the connecting ball of the meter rod.

14. The device of claim 13, wherein the electronic measuring device is a potentiometer having a payout line attached to the catch.

15. A device for measuring cervical dilation comprising:
    a housing including a catch slideably mounted therein;
    a meter rod having a first end and a second end, the second end received by the catch;
    a measuring line attached to the first end of the meter rod; and
    an electronic measuring device mounted to the housing and linked to the catch.

16. The device of claim 15, further comprising a guide tube having a first end and a second end, wherein the first end of the meter rod is received by the guide tube and the measuring line extends from the first end of the guide tube.

17. The device of claim 16, wherein the measuring line is stitched near the first end of the guide tube for receiving a finger tip.

18. The device of claim 16, further comprising a first ring and a second ring, each ring attached to the measuring line near the first end of the guide tube for respectively receiving a finger tip.

19. The device of claim 15, further comprising a visual display in communication with the electronic measuring device.

20. The device of claim 6, further comprising a finger-receiving member associated with the measuring line near the first end of the guide tube for receiving a finger.

21. A device for measuring cervical dilation comprising
    a guide having a first end and a second end;
    a measuring line extending out of a first end of the guide tube;
    an electronic measuring device in communication with the measuring line; and
    a rod having a first end and a second end, the first end of the rod being linked to the measuring line and the second end of the rod being linked to the electronic measuring device, wherein the second end of the rod includes a connecting ball.

22. The device of claim 21, wherein the electronic measuring device is near the second end of the guide tube.

23. The device of claim 21, further comprising a housing adapted to receive the connecting ball.

24. The device of claim 21, further comprising a finger-receiving member associated with measuring line for receiving a finger.

25. The device of claim 24, wherein the finger-receiving member includes a ring attached to the measuring line.

26. The device of claim 25, wherein the first end of the guide tube includes a coned tip.

27. The device of claim 21, further comprising a visual display in communication with the electronic measuring device.

28. The device of claim 21, wherein the measuring line is stitched near the first end of the guide tube for receiving a fingertip.

29. The device of claim 19, wherein the electronic measuring device is a potentiometer.

* * * * *